US00PP21889P2

(12) United States Plant Patent
Smith

(10) Patent No.: US PP21,889 P2
(45) Date of Patent: Apr. 26, 2011

(54) ***SALVIA* PLANT NAMED 'WENDY'S WISH'**

(50) Latin Name: *Salvia×hydrida*
Varietal Denomination: Wendy's Wish

(76) Inventor: Wendy Smith, Rosebud (AU)

( * ) Notice: Subject to any disclaimer, the term of this patent is extended or adjusted under 35 U.S.C. 154(b) by 0 days.

(21) Appl. No.: 12/655,295

(22) Filed: Dec. 29, 2009

Related U.S. Application Data

(60) Provisional application No. 61/205,744, filed on Jan. 23, 2009.

(51) Int. Cl.
*A01H 5/00* (2006.01)

(52) U.S. Cl. ..... Plt./475

(58) Field of Classification Search ..... Plt./475
See application file for complete search history.

*Primary Examiner* — Susan B McCormick Ewoldt

(57) ABSTRACT

A new and distinct cultivar of *Salvia* named 'WENDY'S WISH' that is characterized by medium to high density, strong rigid stems, bright pink flowers, and red-bronze calyces. In combination these traits set 'WENDY'S WISH' apart from all other existing varieties of *Salvia* known to the inventor.

2 Drawing Sheets

Genus: *SALVIA*.
Species: ×*hybrida*.
Denomination: 'WENDY'S WISH'.

BACKGROUND OF THE INVENTION

The present invention relates to a new and distinct cultivar of *SALVIA*, commonly known as sage, and grown as an ornamental perennial plant for garden and landscape. The new cultivar from the family Labiatae is known botanically as *SALVIA×hybrida* and will be referred to hereinafter by the cultivar name 'WENDY'S WISH'.

'WENDY'S WISH' was discovered by the inventor in 2005 as a chance seedling in a cultivated area of the inventor's *Salvia* enthusiast's garden. The inventor selected 'WENDY'S WISH' from amongst a grouping of *Salvia buchananii* and *Salvia chiapensis* 'Purple Majesty'. Selection was based on the criteria of red-bronze calyx color and dense plant habit as the unique traits that distinguish the new cultivar from the parents. As a genus *Salvia* is commonly known to be insect and hummingbird pollinated. 'WENDY'S WISH' resulted from the uncontrolled open cross-pollination of the parents, an individual *Salvia buchananii* (species, unpatented), and an individual *Salvia chiapensis* 'Purple Majesty' (unpatented). Specific male and female parentage is unknown to the inventor.

The distinguishing characteristics of 'WENDY'S WISH' are red-bronze calyx color, bright pink flower color, strong rigid stems, and medium to dense plant density. The closest comparison plant is *Salvia buchananii*, which exhibits green calyx color and sparse plant density. 'WENDY'S WISH' is distinguishable from the comparison plant by calyx color and plant density. 'WENDY'S WISH' is distinguishable from the parent *Salvia* 'Purple Majesty' by flower color.

'WENDY'S WISH' exhibits compact slightly spreading habit, medium to high density, mounding form, medium to dark green leaves, strong rigid purple stems, and from late spring to late summer, a profuse display of bright pink tubular flowers with prominent red-bronze calyces. Flower parts are sweet citrus scented. Mature dimensions of 'WENDY'S WISH' are 80 cm. in height and 80 cm. in width. Cultural requirements include full sun to partial shade, well-draining soil, and minimal water. 'WENDY'S WISH' is hardy to USDA Zone 9.

'WENDY'S WISH' was first asexually propagated by the inventor in 2005 in Rosebud, Victoria, Australia. Asexual propagation was accomplished using softwood tip cuttings. Since that time under careful observation, the distinguishing characteristics of 'WENDY'S WISH' have been determined stable and uniform, and reproduce true to type in successive generations of asexual propagation.

SUMMARY OF THE INVENTION

The distinguishing characteristics of 'WENDY'S WISH' are as follows. In combination these traits set 'WENDY'S WISH' apart from all other existing varieties of *SALVIA* known to the inventor. 'WENDY'S WISH' has not been tested under all possible conditions and phenotypic differences may be observed with variations in environment, climate, and cultural conditions without however any variance in genotype.

1. 'WENDY'S WISH' is perennial in temperatures above 9.4° Centigrade.
2. 'WENDY'S WISH' produces a mounding plant form with medium to high plant density.
3. The stems of 'WENDY'S WISH' are strong and rigid.
4. The flowers of 'WENDY'S WISH' are bright pink in color.
5. The calyces of 'WENDY'S WISH' are prominent and red-bronze in color.
6. 'WENDY'S WISH' blooms from late spring to late summer.
7. 'WENDYS WISH' achieves a height of 80 cm. and a spread of 80 cm.

BRIEF DESCRIPTION OF THE DRAWINGS

The accompanying color drawings illustrate the overall appearance of 'WENDY'S WISH' showing the color of foliage and flowers as true as it is reasonably possible to obtain in color reproductions of this type. Color in the drawings may differ from color values cited in the detailed botanical description, which accurately describe the actual color of 'WENDY'S WISH'. Both drawings were made from an 18-month-old single plant in flower in summer.

The drawing labeled

The drawing labeled

BOTANICAL DESCRIPTION OF THE PLANT

Figure 1:
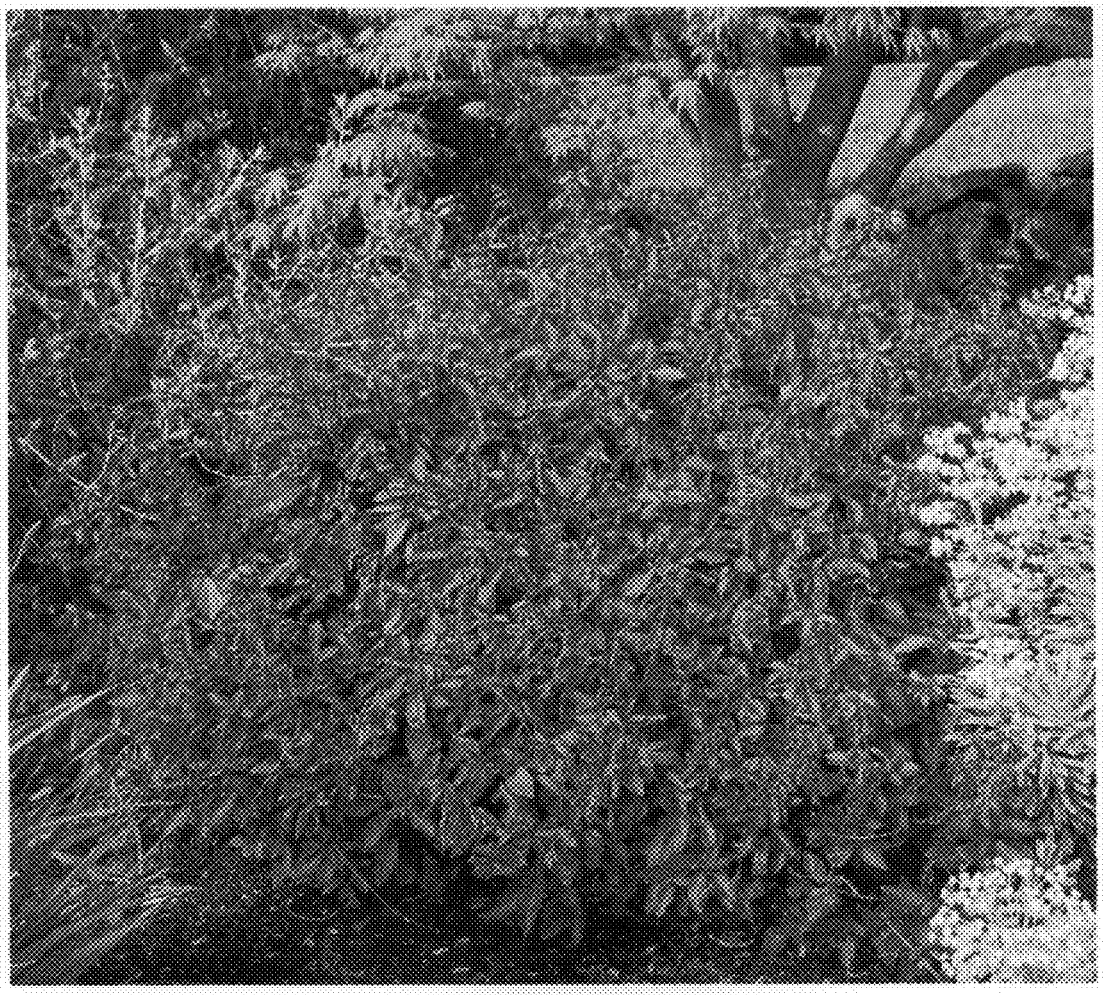
FIG. 1 depicts a single plant of 'WENDY'S WISH' illustrating habit and density.
Figure 2:
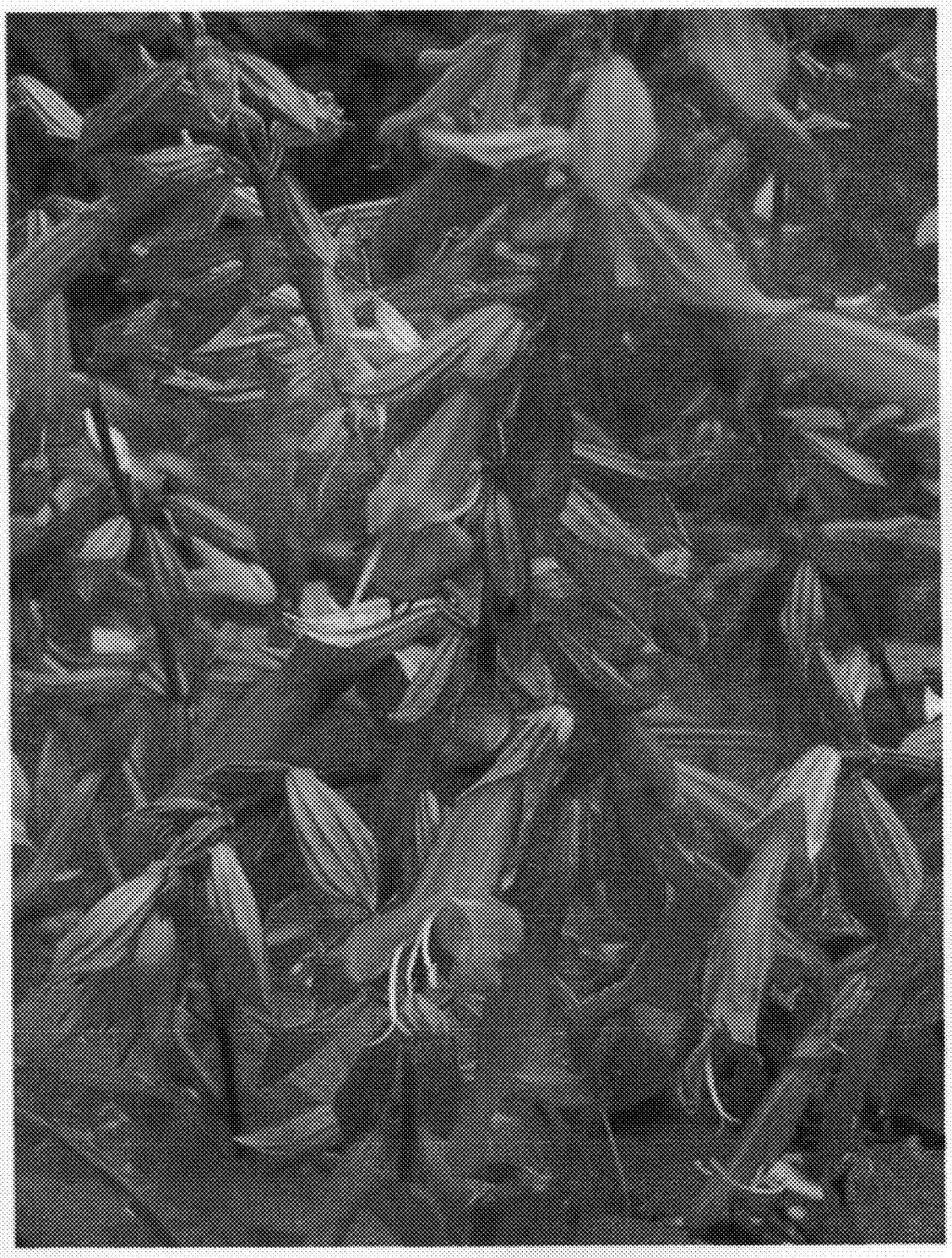
FIG. 2 depicts a close-up view of the flowers of 'WENDY'S WISH' illustrating the bright pink flower color and red-bronze calyces. Drawings were made using conventional techniques and although flower and foliage color may appear different from actual color due to light reflectance, the drawings are as accurate as possible by conventional photography.

The following is a detailed botanical description of 'WENDY'S WISH'. Observations, measurements, values and comparisons were collected in Arroyo Grande, Calif., from 24-month-old plants grown out-of-doors in full sun. Color determinations were made in accordance with The 2001 Royal Horticultural Society Colour Chart from London, England, except where general color terms of ordinary dictionary significance are used. The growing requirements of 'WENDY'S WISH' are similar to the species.

Botanical classification: *SALVIA×hybrida* 'WENDY'S WISH'.
Family: Labiatae.
Genus: *SALVIA*.
Species: *×hybrida*.
Denomination: 'WENDY'S WISH'.
Common name: Sage.
Habit: Compact and slightly spreading.
Form: Mounding.
Density: Medium to dense.
Commercial category: Ornamental.
Use: For garden and landscape.
Suggested commercial container size: 1-liter container.
Parentage: *SALVIA×hybrida* 'WENDY'S WISH' was discovered as a chance seedling resulting from open uncontrolled cross-pollination of the parents, an individual *Salvia buchananii,* and an individual *Salvia chiapensis* 'Purple Majesty' (unpatented). Specific male and female parentage is unknown to the inventor.
Propagation method: Softwood tip cuttings.
Rooting system: Fine and fibrous.
Vigor: Moderate.
Time to root cutting (range): 4-6 weeks.
Crop time (range): 6-9 months to produce a 1-liter container from stem cuttings.
Temperature (range): The recommended air temperature is 20-21° Centigrade.
Dimensions (at maturity): 80 cm. in height and 80 cm. in width.
Cultural requirements: Grow in full sun to partial shade, well-draining soil, with minimal water.
Pest or disease resistance: None known to the inventor.
Pest or disease susceptibility: None known to the inventor.
Hardiness: USDA Zone 9.
Stem:
- *Shape.*—Quadrangular.
- *Surface.*—Fluted and glabrous.
- *Color.*—N186C.
- *Strength.*—Strong and rigid.
- *Length* (*average*).—34 cm.
- *Width* (*average*).—0.45 cm.
- *Internodes* (*average*).—7.30 cm.
- *Fragrance.*—None observed.

Foliage:
- *Type.*—Evergreen.
- *Arrangement.*—Opposite.
- *Division.*—Simple.
- *Margin* (*range*).—Serrate to dentate.
- *Surface* (*abaxial and adaxial*).—Glabrous.
- *Shape.*—Ovate.
- *Length* (*range*).—2 cm. to 9 cm.
- *Width* (*range*).—1 cm. to 6 cm.
- *Abaxial surface color.*—N138B.
- *Adaxial surface color.*—139A.
- *Apex.*—Subacute.
- *Base* (*range*).—Attenuate to aequilateral.
- *Venation pattern.*—Pinnate.
- *Vein color* (*abaxial surface*).—187A.
- *Vein color* (*adaxial surface*).—N138B.
- *Attachment.*—Petiolate.
- *Petiole shape.*—Sulcate.
- *Petiole surface.*—Pubescent.
- *Petiole color.*—187A.
- *Petiole dimensions.*—4.50 cm. in length and 3 mm. in width.
- *Fragrance.*—None observed.

Inflorescence:
- *Inflorescence.*—Raceme.
- *Inflorescence dimensions* (*average*).—24 cm. in length and 4.50 cm. in width.
- *Blooming season* (*range*).—Late spring to late summer.
- *Flower quantity* (*range*).—36 to 66 per peduncle.
- *Persistent or self-cleaning.*—Self-cleaning.
- *Aspect.*—Facing upward and outward.
- *Bud shape.*—Oblanceolate.
- *Bud dimensions.*—2.10 cm. in length and 0.75 cm. in width.
- *Bud color.*—183A.
- *Bud surface.*—Pubescent.
- *Bud apex.*—Subacute.
- *Corolla shape.*—Tubular.
- *Corolla color.*—67A.
- *Corolla dimensions.*—4.50 cm. in depth and 1.50 cm. in diameter.
- *Corolla tube shape.*—Tubular.
- *Corolla tube color.*—67A.
- *Corolla tube dimensions.*—3.25 cm. in depth and 0.70 cm. in diameter.
- *Corolla tube surface* (*dorsal*).—Velutinous.
- *Corolla tube surface* (*ventral*).—Glabrous.
- *Corolla lip.*—2 in number.
- *Lips fused or unfused.*—Basally fused. Upper lip shape: Hooded. Upper lip apex: Emarginate. Upper lip dimensions: 1.25 cm. in length and 0.30 cm. in width. Upper lip color (abaxial and adaxial surface): 67A. Upper lip margin: Velutinous. Upper lip surface (abaxial): Glabrous. Upper lip surface (adaxial): Velutinous. Lower lip shape: 3-Lobed. Lobe apex: Obtuse. Lower lip dimensions: 1.10 cm. in length and 1.30 cm. in width. Lower lip color (abaxial and adaxial surfaces): 67A. Lobe margin: Entire. Lobe surface (abaxial): Velutinous. Lobe surface (adaxial): Glabrous. Lobes fused or unfused: Basally fused.
- *Calyx shape* (*range*).—Ovoid to bell-shaped.

*Calyx dimensions.*—2.25 cm. in length and 0.75 cm. in width.
*Calyx surface* (*dorsal and ventral*).—Pubescent and fluted.
*Calyx color* (*range on dorsal and ventral surface*).—182B to 183A.
*Sepals.*—3 in number.
*Sepals fused or unfused.*—Fused.
*Sepal apex.*—Acute.
*Sepal color* (*range on dorsal and ventral surface*).—182B to 183A.
*Sepal margin.*—Entire.
*Pedicel color.*—183A.
*Pedicel surface.*—Villous.
*Pedicel dimensions* 0.60 cm. in length and <1 mm. in width.
*Peduncle color.*—N186C.
*Peduncle dimensions* (*average*).—30 cm. in length and 2 mm. in width.
*Peduncle shape.*—Quadrangular and fluted.
*Peduncle surface.*—Pubescent.
*Internode length.*—3 cm.
*Flower fragrance.*—Sweet citrus scented.
*Lastingness of flower* (*range*).—5-7 days.

Reproductive organs:
*Stamen quantity.*—2 in number.
*Stamen length.*—6 mm.
*Stamen color.*—N155C.
*Staminode color.*—181A.
*Staminode length.*—3 mm.
*Pollen.*—Absent.
*Pistil quantity.*—1 in number.
*Pistil length.*—5 cm.
*Pistil color* (*range*).—67C to N155B.
*Style shape:.*—2-lobed.
*Style color.*—71D.
*Style dimensions.*—4 mm. in length and 6 mm. in width.
*Ovary position.*—Superior.
*Ovary shape.*—Globose.
*Ovary dimensions.*—3 mm. in height and 3 mm. in diameter.
*Ovary color.*—195A.
*Ovary surface.*—Glabrous.
*Ovary appearance.*—Semi-glossy.
*Seed.*—None found.

The invention claimed is:

1. A new and distinct cultivar of *Salvia* plant named 'WENDY'S WISH' as described and illustrated herein.

* * * * *